US010081610B2

(12) United States Patent
Song et al.

(10) Patent No.: US 10,081,610 B2
(45) Date of Patent: Sep. 25, 2018

(54) EFFICIENT AND SCALABLE SYNTHESIS OF 2-(1'H-INDOLE-3'-CARBONYL)-THIAZOLE-4-CARBOXYLIC ACID METHYL ESTER AND ITS STRUCTURAL ANALOGS

(71) Applicant: ARIAGEN, INC., Menlo Park, CA (US)

(72) Inventors: Jiasheng Song, Madison, WI (US); Suoming Zhang, Shanghai (CN); Guodong Li, Shanghai (CN); Luquing Yang, Shanghai (CN)

(73) Assignee: ARIAGEN, INC., Menlo Park, CA (US)

( * ) Notice: Subject to any disclaimer, the term of this patent is extended or adjusted under 35 U.S.C. 154(b) by 0 days.

(21) Appl. No.: 15/509,722

(22) PCT Filed: Sep. 10, 2015

(86) PCT No.: PCT/US2015/049302
§ 371 (c)(1),
(2) Date: Mar. 8, 2017

(87) PCT Pub. No.: WO2016/040553
PCT Pub. Date: Mar. 17, 2016

(65) Prior Publication Data
US 2017/0291881 A1    Oct. 12, 2017

Related U.S. Application Data

(60) Provisional application No. 62/049,804, filed on Sep. 12, 2014.

(51) Int. Cl.
*C07D 277/20* (2006.01)
*C07D 209/12* (2006.01)
*C07D 417/06* (2006.01)
*C07B 43/08* (2006.01)
*C07C 67/47* (2006.01)

(52) U.S. Cl.
CPC ......... *C07D 277/20* (2013.01); *C07D 209/12* (2013.01); *C07D 417/06* (2013.01); *C07B 43/08* (2013.01); *C07C 67/47* (2013.01)

(58) Field of Classification Search
CPC .................................................. C07D 277/20
USPC ...................................................... 546/270.1
See application file for complete search history.

(56) References Cited

U.S. PATENT DOCUMENTS

2002/0177594 A1   11/2002  Curtin et al.

FOREIGN PATENT DOCUMENTS

| WO | 98/39330 A1 | 9/1998 |
| WO | 03/068742 A1 | 8/2003 |
| WO | 2004/060888 A1 | 7/2004 |
| WO | 2006/029862 A1 | 3/2006 |
| WO | 2013/033003 A1 | 3/2013 |
| WO | 2013/041468 A1 | 3/2013 |

OTHER PUBLICATIONS

Ozawa et al., "A new synthesis of glutathione via the thiazoline peptide," Bulletin of the Chemical Society of Japan 53 (9):2592-2593 (1980).
Akahoshi et al., "Synthesis, structure-activity relationships, and pharmacokinetic profiles of nonpeptidic .alpha.-keto heterocycles as novel inhibitors of human chymase," Journal of Medicinal Chemistry 44(8):286-1296 (2001).
Johnson et al.,"Total Synthesis of (−)-Rhazinilam: Asymmetric C-H Bond Activation via the Use of a Chiral Auxiliary," Journal of the American Chemical Society 124(24):6900-6903 (2002). Johnson et al., "Total Synthesis of (−)-Rhazinilam: Asymmetric C-H Bond Activation via the Use of a Chiral Auxiliary (Supporting information)," Journal of the American Chemical Society pp. S1-S4 (2002).
Van Zandt et al., "Discovery of 3-[(4,5,7-Trifluorobenzothiazol-2-yl)methyl]indole-N-acetic Acid (Lidorestat) and Congeners as Highly Potent and Selective Inhibitors of Aldose Reductase for Treatment of Chronic Diabetic complications," Journal of Medicinal Chemistry 48(9):3141-3152 (2005).
Fuganti et al., "A general method for the synthesis of the most powerful naturally occurring Maillard flavors," Tetrahedron 63(22):4762-4767 (2007).
Mizzoni et al., "Some thiazolines and thiazolidinones with antituberculous activity," Journal of the American Chemical Society 80:3471-3475 (1958).
Solankee et al., "Thiazolines: synthesis and antitubercular activity of 2-alkyl/aryl/-5-(.omega.-carboxypentyl)-.DELTA.2-thiazolin-4-one. Part II," Journal of the Institution of Chemists (India) 66:47-48 (1994).
Narender M et al., "Aqueous phase synthesis of thiazoles and aminothiazoles in the presence of beta-cyclodextrin," Tetrahedron Letters 46:5953-5955 (2005).
Milinkevich et al., "Synthesis of 5-(Thiazol-5-yl)-4,5-dihydroisoxazoles from 3-Chloropentane-2,4-dione," Journal of Combinatorial Chemistry 10(4):521-525 (2008).
Heravi et al., "An efficient synthesis of thiazol-2-imine derivatives via a one-pot, three-component reaction," Tetrahedron Letters 53(4):392-394 (2012).
Mjambili et al., "Synthesis and biological evaluation of 2-aminothiazole derivatives as antimycobacterial and antiplasmodial agents," Bioorganic & Medicinal Chemistry Letters 24(2):560-564 (2014).
Bankoti et al., "Functional and phenotypic effects of AhR activation in inflammatory dendritic cells," Toxicol Appl Pharmacol 246:18-28 (2010).
Cheng et al., "Tryptophan derivatives regulate the transcription of Oct4 in stem-like cancer cells." Nat Commun 6:7209 (2015).

(Continued)

*Primary Examiner* — Taofiq A Solola
(74) *Attorney, Agent, or Firm* — Steptoe & Johnson LLP; Harold H. Fox; Dong I. Chen

(57) ABSTRACT

Methods of synthesizing 2-(1'H-indole-3'-carbonyl)-thiazole-4-carboxylic acid methyl ester (ITE) and structural analogs thereof. The methods include condensation reactions or condensation and oxidation reactions to form the thiazoline or thiazole moiety of ITE or its structural analogs.

25 Claims, 1 Drawing Sheet

(56) References Cited

OTHER PUBLICATIONS

Duarte et al., "Differential influences of the aryl hydrocarbon receptor on Th17 mediated responses in vitro and in vivo," PLoS One 8:e79819 (2013).

Forrester et al., "Induction of a chloracne phenotype in an epidermal equivalent model by 2,3,7,8-tetrachlorodibenzo-p-dioxin (TCDD) is dependent on aryl hydrocarbon receptor activation and is not reproduced by aryl hydrocarbon receptor knock down," J Dermatol Sci 73:10-22 (2014).

Hao et al., "Inhibitory effect and its mechanism of ITE, an endogenous aryl hydrocarbon receptor (AhR) ligand, on the proliferation of human placental trophoblast cells," Fudan Univ J Med Sci 41:488-493 (2014).

Henry et al., "A potential endogenous ligand for the aryl hydrocarbon receptor has potent agonist activity in vitro and in vivo," Archives of Biochemistry and Biophysics 450:67-77 (2006).

Henry et al., "TCDD and a Putative Endogenous AhR Ligand, ITE, Elicit the Same Immediate Changes in Gene Expression in Mouse Lung Fibroblasts," Toxicological Sciences 114:90-100 (2010).

Kang et al., "Genome-wide transcriptional profiling of human glioblastoma cells in response to ITE treatment," Genomics Data 5:281-283 (2015).

Lehmann et al.,"The Aryl Hydrocarbon Receptor Ligand ITE Inhibits TGFβ1-Induced Human Myofibroblast Differentiation," Am J Pathol 178(4):1556-1567 (2011).

Nugent et al., "ITE, A Novel Endogenous Nontoxic Aryl Hydrocarbon Receptor Ligand, Efficiently Suppresses EAU and T-Cell—Mediated Immunity," Invest Ophthalmol Vis Sci 54:7463-7469 (2013).

Quintana et al., "Control of Treg and TH17 cell differentiation by the aryl hydrocarbon receptor," Nature 453:65-71 (2008).

Quintana et al., "An endogenous aryl hydrocarbon receptor ligand acts on dendritic cells and T cells to suppress experimental autoimmune encephalomyelitis," Proc Natl Acad Sci U S A 107:20768-73 (2010).

Schulz et al., "Activation of the aryl hydrocarbon receptor suppresses sensitization in a mouse peanut allergy model," Toxicol Sci 123:491-500 (2011).

Simones et al., "Consequences of AhR Activation in Steady-State Dendritic Cells," Toxicological Sciences 119:293-307 (2011).

Song et al., "A ligand for the aryl hydrocarbon receptor isolated from lung," Proc Natl Acad Sci U S A 99:14694-9 (2002).

Tsai et al., "Aryl hydrocarbon receptor (AhR) agonists increase airway epithelial matrix metalloproteinase activity," J Mol Med 92:615-628 (2014).

Wang et al., "An endogenous aryl hydrocarbon receptor ligand inhibits proliferation and migration of human ovarian cancer cells," Cancer Lett 340:63-71 (2013).

Wang et al., "Activation of the aryl hydrocarbon receptor affects activation and function of human monocyte-derived dendritic cells," Clinical and Experimental Immunology 177:521-530 (2014).

Wang et al., "Decreased Expression of the Aryl Hydrocarbon Receptor in Ocular Behcet's Disease," Mediators Inflamm 2014:195094 (2014).

Wei et al., "Role of the Aryl Hydrocarbon Receptor in the Pathogenesis of Chronic Rhinosinusitis with Nasal Polyps," Inflammation 37:387-95 (2013).

Wei et al., "An aryl hydrocarbon receptor ligand acts on dendritic cells and T cells to suppress the Th17 response in allergic rhinitis patients," Laboratory Investigation 94:528-535 (2014).

Wei et al., "Increased aryl hydrocarbon receptor expression in patients with allergic rhinitis," QJM 107:107-113 (2014).

Wu et al., "ITE and TCDD Differentially Regulate the Vascular Remodeling of Rat Placenta via the Activation of AhR," PLoS One 9:e86549 (2014).

Yeste et al., "Nanoparticle-mediated codelivery of myelin antigen and a tolerogenic small molecule suppresses experimental autoimmune encephalomyelitis," Proc Natl Acad Sci U S A 109:11270-5 (2012).

Yoshida et al., "Effects of AhR ligands on the production of immunoglobulins in purified mouse B cells," Biomedical Research 33:67-74 (2012).

Zhao et al., "Akt-mediated phosphorylation of Oct4 is associated with the proliferation of stem-like cancer cells," Oncology Reports 33:1621-1629 (2015).

A.
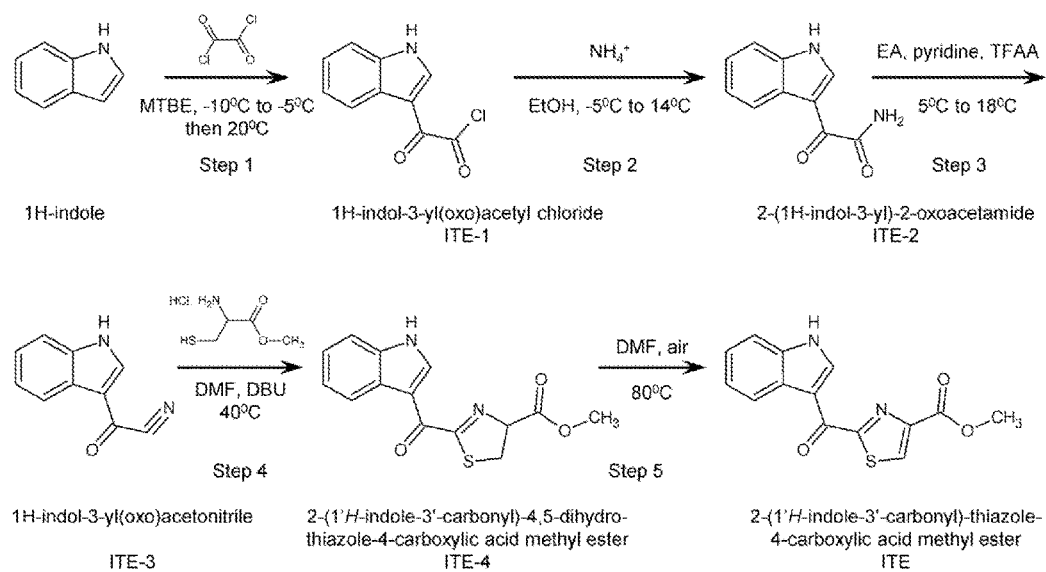
B.
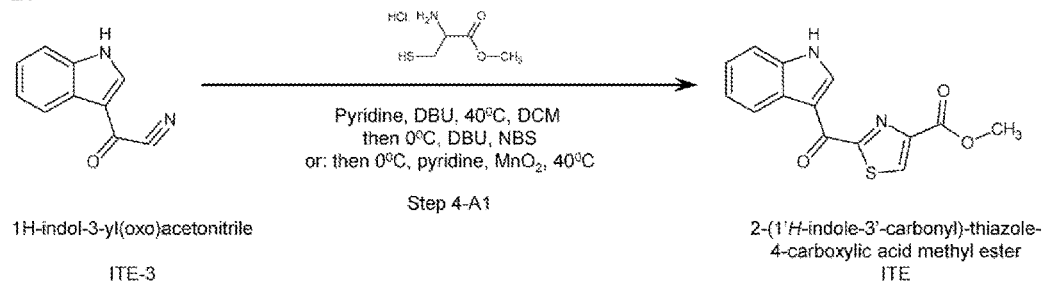
C.
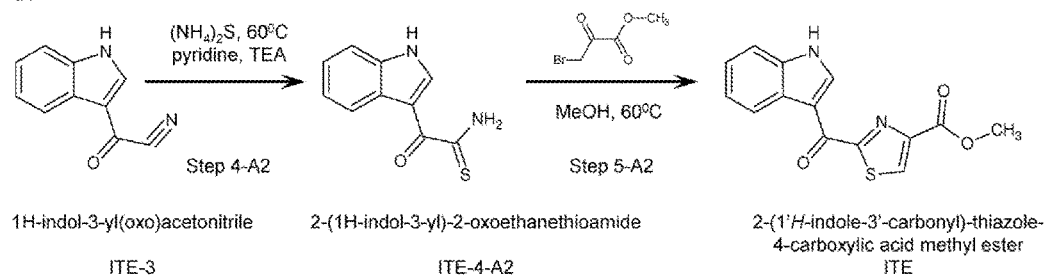

EFFICIENT AND SCALABLE SYNTHESIS OF 2-(1'H-INDOLE-3'-CARBONYL)-THIAZOLE-4-CARBOXYLIC ACID METHYL ESTER AND ITS STRUCTURAL ANALOGS

FIELD OF THE INVENTION

The invention is directed to the synthesis of 2-(1'H-indole-3'-carbonyl)-thiazole-4-carboxylic acid methyl ester and structural analogs thereof.

BACKGROUND

The aryl hydrocarbon receptor (Ah receptor or AhR) is a ligand-inducible transcription factor that mediates a number of important biological and pharmacological processes. 2-(1'H-Indole-3'-carbonyl)-thiazole-4-carboxylic acid methyl ester (ITE) (Song et al. 2002, U.S. Pat. No. 6,916,834) is an endogenous ligand for the receptor. ITE can be used to study AhR-mediated biological processes and therapeutic potentials and to treat disorders such as cancer (US 2012/0214853, U.S. Pat. No. 8,604,067, Wang et al. 2013, Cheng et al. 2015), obesity (U.S. Pat. No. 7,419,992), and conditions related to imbalanced actions of the immune system (Quintana et al. 2010, Nugent et al. 2013).

The original ITE synthesis scheme (Grzywacz et al. 2003, U.S. Pat. No. 7,002,019) provided for small-scale synthesis of ITE for initial confirmation of its structural identification (Song et al. 2002, U.S. Pat. No. 6,916,834) and for laboratory-scale biomedical studies. However, the original synthesis scheme is not capable of efficiently producing ITE at levels required for clinical studies in large animals and human subjects or therapies.

The efficiency of intra-molecular cyclization to form a thiazoline ring in the original ITE synthesis scheme (Grzywacz et al. 2003, U.S. Pat. No. 7,002,019) is extremely low and becomes even lower as its synthetic scale increases. The inefficiency of this key step severely limits the efficiency of the entire synthesis. The intra-molecular cyclization is most probably hindered by a neighboring carbonyl group. Due to the presence of the carbonyl group, success using other cyclization reactions is unpredictable.

A new synthesis that efficiently forms a thiazoline or thiazole ring is needed in order to develop an efficient and scalable process for large-scale production of ITE and its structural analogs.

SUMMARY OF THE INVENTION

Disclosed herein are methods of synthesizing 2-(1'H-indole-3'-carbonyl)-thiazole-4-carboxylic acid methyl ester (ITE) and its structural analogs using very efficient condensations of intermediates to form frameworks containing, for example, moieties of indoles and thiazolines or indoles and thiazoles. The methods disclosed herein eliminate the bottleneck present in the original synthesis scheme, thereby dramatically increasing the efficiency and scalability of synthesis. In addition, the methods disclosed herein are safe and controllable, employ mild conditions for all reaction steps, and employ readily available, low-cost materials and reagents.

Disclosed herein is a method comprising condensing a compound of Formula II:

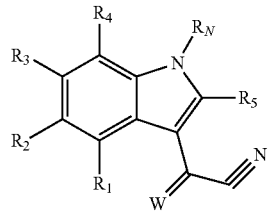

or a salt thereof,
with a compound of Formula III:

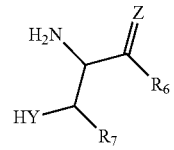

or a salt thereof,
to yield a compound of Formula IV:

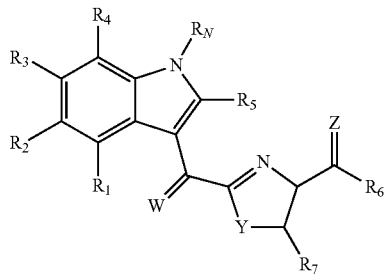

or a salt thereof.

In Formulas II, III, and IV, the substituents W, Y, and Z are each independently selected from the group consisting of oxygen (O) and sulfur (S). $R_1$, $R_2$, $R_3$, $R_4$, $R_5$, $R_6$, $R_7$, and $R_N$ are each independently selected from the group consisting of hydrogen, deuterium, halo, amino, hydroxy, cyano, formyl, nitro, alkyl, haloalkyl, alkenyl, haloalkenyl, alkynyl, haloalkynyl, alkoxy, haloalkoxy, thioalkoxy, halothioalkoxy, alkanoyl, haloalkanoyl, thioalkanoyl, halothioalkanoyl, carbonyloxy, halocarbonyloxy, carbonylthio, halocarbonylthio, thiocarbonyloxy, halothiocarbonyloxy, thiocarbonylthio, halothiocarbonylthio, and —$S(O)_nR_8$ (n=0 to 2, $R_8$ is directly connected to S), wherein $R_8$ is selected from the group consisting of hydrogen, deuterium, halo, amino, hydroxy, thiol, cyano, formyl, alkyl, haloalkyl, alkenyl, haloalkenyl, alkynyl, haloalkynyl, alkoxy, haloalkoxy, thioalkoxy, halothioalkoxy, alkanoyl, haloalkanoyl, thioalkanoyl, halothioalkanoyl, carbonyloxy, halocarbonyloxy, carbonylthio, halocarbonylthio, thiocarbonyloxy, halothiocarbonyloxy, thiocarbonylthio, and halothiocarbonylthio, except that $R_N$ may further be selected from an amino protecting group. The condensing is preferably conducted in the presence of an aprotic solvent. The condensing is preferably conducted in the presence of a base.

The above-described method may optionally comprise oxidizing the compound of Formula IV to yield a compound of Formula I:

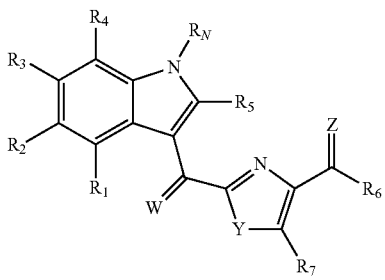

(I)

or a salt thereof.

In Formula I, the subsituents are as described above for Formulas II, III, and IV.

In some versions, the oxidizing step used to yield the compound of Formula I is conducted without substantial isolation of the compound of Formula IV from the reaction mixture in which the compound of Formula IV was synthesized.

In some versions, the oxidizing step used to yield the compound of Formula I comprises adding an oxidant directly to the reaction mixture or a diluted reaction mixture comprising the reaction mixture diluted with solvent.

In some versions, the method further comprises, after the condensing step and prior to the oxidizing step, diluting the reaction mixture by an amount of at least about 2-fold.

In some versions, the method further comprises, after the condensing step and prior to the oxidizing step, cooling the reaction mixture or a diluted reaction mixture comprising the reaction mixture diluted with solvent from a condensation reaction temperature at which the condensing is conducted to a cooled temperature. The cooled temperature may be at least about 10° C. lower than the condensation reaction temperature.

In some versions, the method further comprises adding an oxidant to the reaction mixture or the diluted reaction mixture when the reaction mixture or the diluted reaction mixture is at the cooled temperature.

In some versions, the oxidizing is conducted at the cooled temperature.

In some versions, the method further comprises, after the cooling, heating the reaction mixture or the diluted reaction mixture from the cooled temperature to a heated temperature and conducting the oxidizing at the heated temperature. In some versions, the heated temperature may be at least about 10° C. higher than the cooled temperature.

Also disclosed herein is a method comprising condensing a compound of Formula V:

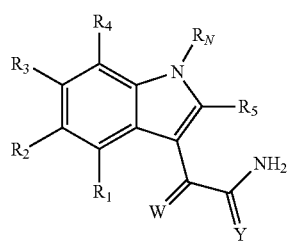

(V)

or a salt thereof, with a compound of Formula VI:

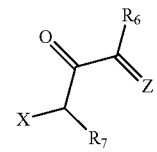

(VI)

or a salt thereof,
to yield a compound of Formula I:

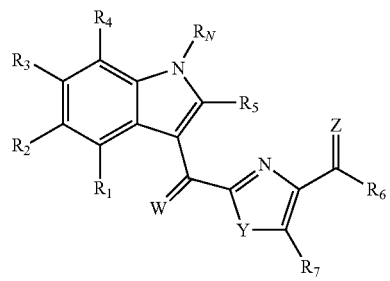

(I)

or a salt thereof.

In Formulas V, VI, and I, X is a leaving group, such as a leaving group selected from the group consisting of chlorine (Cl), bromine (Br), iodine (I), —OS(O)$_2$CH$_3$, and —OS(O)$_2$C$_6$H$_4$CH$_3$. W, Y, and Z are each independently selected from the group consisting of oxygen (O) and sulfur (S). R$_1$, R$_2$, R$_3$, R$_4$, R$_5$, R$_6$, R$_7$, and R$_N$ are each independently selected from the group consisting of hydrogen, deuterium, halo, amino, hydroxy, cyano, formyl, nitro, alkyl, haloalkyl, alkenyl, haloalkenyl, alkynyl, haloalkynyl, alkoxy, haloalkoxy, thioalkoxy, halothioalkoxy, alkanoyl, haloalkanoyl, thioalkanoyl, halothioalkanoyl, carbonyloxy, halocarbonyloxy, carbonylthio, halocarbonylthio, thiocarbonyloxy, halothiocarbonyloxy, thiocarbonylthio, halothiocarbonylthio, and —S(O)$_n$R$_8$ (n=0 to 2, R$_8$ is directly connected to S), wherein R$_8$ is selected from the group consisting of hydrogen, deuterium, halo, amino, hydroxy, thiol, cyano, formyl, alkyl, haloalkyl, alkenyl, haloalkenyl, alkynyl, haloalkynyl, alkoxy, haloalkoxy, thioalkoxy, halothioalkoxy, alkanoyl, haloalkanoyl, thioalkanoyl, halothioalkanoyl, carbonyloxy, halocarbonyloxy, carbonylthio, halocarbonylthio, thiocarbonyloxy, halothiocarbonyloxy, thiocarbonylthio, and halothiocarbonylthio, except that R$_N$ may further be selected from an amino protecting group.

The objects and advantages of the method will appear more fully from the following detailed description of the preferred embodiment of the invention made in conjunction with the accompanying drawings.

BRIEF DESCRIPTION OF THE DRAWING

FIG. 1 shows schema of exemplary methods of synthesizing the exemplary compound 2-(1'H-indole-3'-carbonyl)-thiazole-4-carboxylic acid methyl ester (ITE). Scheme A shows a method of synthesizing ITE from 1H-indole via a number of intermediates. Scheme B shows methods of synthesizing ITE from 1H-indol-3-yl(oxo)acetonitrile (ITE-3) in one container ("one-pot") without purification of intermediate 2-(1'H-indole-3'-carbonyl)-4,5-dihydro-thiazole-4-carboxylic acid methyl ester (ITE-4). Scheme C shows a method of synthesizing ITE from ITE-3 via intermediate 2-(1H-indol-3-yl)-2-oxoethanethioamide (ITE-4-A2). MTBE, methyl tert-butyl ether. EtOH, ethanol. EA, ethyl acetate. TFAA, trifluroacetic anhydride. DMF, dimethylformamide. DBU, 1,8-diazabicyclo[5.4.0]undec-7-ene. DCM, dicholoromethane. NBS, N-bromosuccinimide TEA, trimethylamine MeOH, methanol.

DETAILED DESCRIPTION OF THE INVENTION

All technical and scientific terms used herein are the same as those commonly used by those ordinary skilled in the art to which the present invention pertains unless defined specifically otherwise.

"ITE" stands for 2-(1'H-indole-3'-carbonyl)-thiazole-4-carboxylic acid methyl ester, an endogenous ligand for a receptor named aryl hydrocarbon receptor (Ah receptor, or AhR).

"Structural analog" or simply "analog" of ITE refers to any compound with a chemical structure similar to that of ITE. Examples of structural analogs include compounds having the same carbon backbone but having different substitutions on the carbons in the carbon backbone or having different degrees of saturation of the carbons in the carbon backbone.

"Hydroxy", "thiol", "cyano", "nitro", and "formyl" refer, respectively, to —OH, —SH, —CN, —NO$_2$, and —CHO.

"Alkyl" refers to a group of one (1) to eight (8) hydrogen-saturated carbons connected in linear, branched, or cyclic fashion, including the combination in linear, branched, and cyclic connectivity.

"Halo" refers to any of halogen atoms fluorine (F), chlorine (Cl), bromine (Br), or iodine (I).

"Haloalkyl" refers to an alkyl substituted by one or more halo(s).

"Alkenyl" refers to a group of hydrocarbons containing two (2) to eight (8) carbons, which are linear, branched, cyclic, or in combination thereof, with at least one carbon-to-carbon double bond.

"Haloalkenyl" refers to an alkenyl substituted by one or more halo(s).

"Alkynyl" refers to a group of hydrocarbons containing two (2) to eight (8) carbons, which are linear, branched, cyclic, or in combination thereof, with at least one carbon-to-carbon triple bond.

"Haloalkynyl" refers to an alkynyl substituted by one or more halo(s).

"Amino protecting group" represents any group commonly used for the protection of amino functions. Such protecting groups are discussed by P. G. M. Wuts in "Protective Groups in Organic Synthesis, 5$^{th}$ Edition" John Wiley and Sons, Inc., New York, ©2014, ISBN-13: 978-1118057483, which is incorporated herein by reference in its entirety. Exemplary amino protecting groups include alkyl carbamates, moieties of corresponding amides, etc., such as allyl carbamate (Alloc), t-butyl carbamate (BOC), 9-fluorenylmethyl carbamate (FMOC), benzyl carbamate (Cbz), acetamide, chloroacetamide, trifluoroacetamide (TFA), phthalimide, benzylamine, triphenylmethylamine (tritylamine), benzylideneamine, p-toluenesulfonamide, tosylamide, etc.

"Amino" refers to —NR$_a$R$_b$, wherein R$_a$ and R$_b$, both directly connected to the N, can be independently selected from hydrogen, deuterium, halo, hydroxy, cyano, formyl, nitro, alkyl, haloalkyl, alkenyl, haloalkenyl, alkynyl, haloalkynyl, alkoxy, haloalkoxy, thioalkoxy, halothioalkoxy, alkanoyl, haloalkanoyl, thioalkanoyl, halothioalkanoyl, carbonyloxy, halocarbonyloxy, carbonylthio, halocarbonylthio, thiocarbonyloxy, halothiocarbonyloxy, thiocarbonylthio, halothiocarbonylthio, a nitrogen protective group, or —S(O)$_n$R$_c$ (n=0 to 2, R$_c$ is directly connected to S), wherein R$_c$ is independently selected from hydrogen, deuterium, halo, amino, hydroxy, thiol, cyano, formyl, alkyl, haloalkyl, alkenyl, haloalkenyl, alkynyl, haloalkynyl, alkoxy, haloalkoxy, thioalkoxy, halothioalkoxy, alkanoyl, haloalkanoyl, thioalkanoyl, halothioalkanoyl, carbonyloxy, halocarbonyloxy, carbonylthio, halocarbonylthio, thiocarbonyloxy, halothiocarbonyloxy, thiocarbonylthio, or halothiocarbonylthio.

"Alkoxy" refers to an alkyl connected to an oxygen atom (—O-alkyl).

"Haloalkoxy" refers to a haloalkyl connected to an oxygen atom (—O-haloalkyl).

"Thioalkoxy" refers to an alkyl connected to a sulfur atom (—S-alkyl).

"Halothioalkoxy" refers to a haloalkyl connected to a sulfur atom (—S-haloalkyl).

"Carbonyl" refers to —(CO)—, wherein (CO) indicates that the oxygen is connected to the carbon with a double bond.

"Alkanoyl (or acyl)" refers to an alkyl connected to a carbonyl group [—(CO)-alkyl].

"Haloalkanoyl (or haloacyl)" refers to a haloalkyl connected to a carbonyl group [—(CO)-haloalkyl].

"Thiocarbonyl" refers to —(CS)—, wherein (CS) indicates that the sulfur is connected to the carbon with a double bond.

"Thioalkanoyl (or thioacyl)" refers to an alkyl connected to a thiocarbonyl group [—(CS)-alkyl].

"Halothioalkanoyl (or halothioacyl)" refers to a haloalkyl connected to a thiocarbonyl group [—(CS)-haloalkyl].

"Carbonyloxy" refers to an alkanoyl (or acyl) connected to an oxygen atom [—O—(CO)-alkyl].

"Halocarbonyloxy" refers to a haloalkanoyl (or haloacyl) connected to an oxygen atom [—O—(CO)-haloalkyl].

"Carbonylthio" refers to an alkanoyl (or acyl) connected to a sulfur atom [—S—(CO)-alkyl].

"Halocarbonylthio" refers to a haloalkanoyl (or haloacyl) connected to a sulfur atom [—S—(CO)-haloalkyl].

"Thiocarbonyloxy" refers to a thioalkanoyl (or thioacyl) connected to an oxygen atom [—O—(CS)-alkyl].

"Halothiocarbonyloxy" refers to a halothioalkanoyl (or halothioacyl) connected to an oxygen atom [—O—(CS)-haloalkyl].

"Thiocarbonylthio" refers to a thioalkanoyl (or thioacyl) connected to a sulfur atom [—S—(CS)-alkyl].

"Halothiocarbonylthio" refers to a halothioalkanoyl (or halothioacyl) connected to a sulfur atom [—S—(CS)-haloalkyl].

One aspect of the invention comprises a method of synthesizing a compound of Formula IV by condensing a compound of Formula II with a compound of Formula III.

Formula IV is:

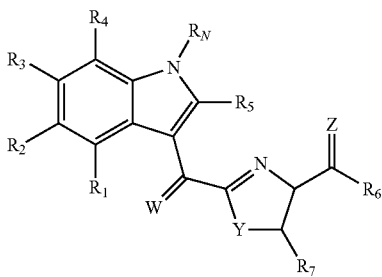

or a salt thereof,
wherein:
W, Y, and Z are each independently selected from the group consisting of oxygen (O) and sulfur (S); and
$R_1$, $R_2$, $R_3$, $R_4$, $R_5$, $R_6$, $R_7$, and $R_N$ are each independently selected from the group consisting of hydrogen, deuterium, halo, amino, hydroxy, cyano, formyl, nitro, alkyl, haloalkyl, alkenyl, haloalkenyl, alkynyl, haloalkynyl, alkoxy, haloalkoxy, thioalkoxy, halothioalkoxy, alkanoyl, haloalkanoyl, thioalkanoyl, halothioalkanoyl, carbonyloxy, halocarbonyloxy, carbonylthio, halocarbonylthio, thiocarbonyloxy, halothiocarbonyloxy, thiocarbonylthio, halothiocarbonylthio, and —S(O)$_n$R$_8$ (n=0 to 2, $R_8$ is directly connected to S), wherein $R_8$ is selected from the group consisting of hydrogen, deuterium, halo, amino, hydroxy, thiol, cyano, formyl, alkyl, haloalkyl, alkenyl, haloalkenyl, alkynyl, haloalkynyl, alkoxy, haloalkoxy, thioalkoxy, halothioalkoxy, alkanoyl, haloalkanoyl, thioalkanoyl, halothioalkanoyl, carbonyloxy, halocarbonyloxy, carbonylthio, halocarbonylthio, thiocarbonyloxy, halothiocarbonyloxy, thiocarbonylthio, and halothiocarbonylthio, except that $R_N$ may further be selected from an amino protecting group.

Formula II is:

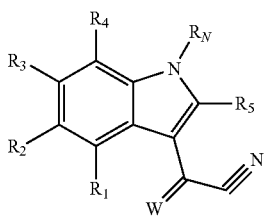

or a salt thereof,
wherein $R_1$-$R_5$, $R_N$, and W are as defined above for Formula IV.

Formula III is:

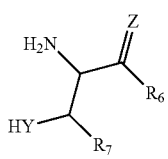

or a salt thereof, wherein $R_6$, $R_7$, Y and Z are as defined above for Formula IV.

The synthesis of a compound of Formula IV by condensing the compound of Formula II with the compound of Formula III is shown below in Scheme 1:

Scheme 1

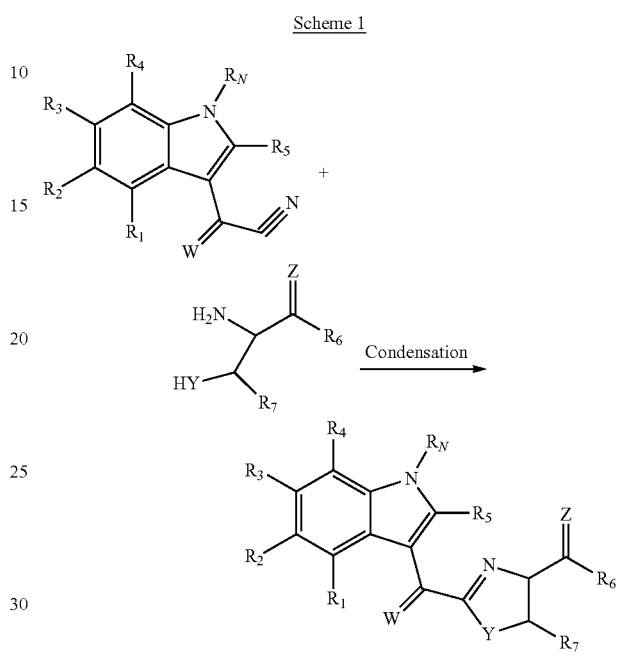

The condensation of Scheme 1 is preferably conducted in the presence of a base. The base may be any base, such as a Brønsted-Lowery base or a Lewis base, but is preferably a Brønsted-Lowery base. The base is preferably a non-nucleophilic base. Exemplary bases include 1,8-diazabicyclo[5.4.0]undec-7-ene (DBU), NaHCO$_3$, Na$_2$CO$_3$, triethylamine (TEA), potassium tert-butoxide, sodium tert-butoxide pyridine, potassium carbonate, sodium hydroxide, sodium hydride, potassium hydride, N,N-diisopropylethylamine (DIPEA), phosphazene bases, such as t-Bu-P4, lithium diisopropylamide (LDA), silicon-based amides, such as sodium and potassium bis(trimethylsilyl)amide (NaHMDS and KHMDS, respectively), lithium tetramethylpiperidide (LiTMP), and 2,6-di-tert-butylpyridine, among others. 1,8-Diazabicyclo[5.4.0]undec-7-ene, NaHCO$_3$, Na$_2$CO$_3$, triethylamine are preferred. 1,8-Diazabicyclo[5.4.0]undec-7-ene and NaHCO$_3$ are particularly preferred.

The condensation of Scheme 1 is preferably conducted in a non-aqueous solvent. The non-aqueous solvent is preferably an aprotic solvent. Exemplary aprotic solvents include dimethylformamide (N,N-dimethylformamide) (DMF), dimethyl sulfoxide (DMSO), pyridine, dioxane, dichloromethane, perfluorohexane, α,α,α-trifluorotoluene, pentane, hexane, cyclohexane, methylcyclohexane, decalin, carbon tetrachloride, freon-11, benzene, dicholoromethane, toluene, triethyl amine, carbon disulfide, diisopropyl ether, diethyl ether (ether), t-butyl methyl ether, chloroform, ethyl acetate, 1,2-dimethoxyethane (glyme), 2-methoxyethyl ether (diglyme), tetrahydrofuran (THF), methylene chloride, 2-butanone, acetone, hexamethylphosphoramide, N-methylpyrrolidinone, nitromethane, acetonitrile, sulfolane, and propylene carbonate. Dimethylformamide, dimethyl sulfoxide, pyridine, and dioxane are preferred. Dimethylformamide, dimethyl sulfoxide, and pyridine are particularly preferred. As used herein, "solvent" encompasses any singular solvent or mixture of solvents.

The condensation of Scheme 1 is preferably conducted at a temperature of from about 0° C. to about 85° C., such as from about 10° C. to about 75° C., from about 20° to about 70° C., from about 30° C. to about 70° C., from about 35° C. to about 65° C., or from about 40° C. to about 60° C.

The condensation of Scheme 1 is preferably conducted for a period of at least about 0.5, about 1, about 2, about 3, about 4 hours, or more and/or up to about 6 hours, about 7 hours, about 8 hours, about 9 hours, about 10 hours, about 15 hours, about 20 hours, about 25 hours, about 30 hours, about 40 hours or more. In some versions, the condensation of Scheme I is conducted for a period of from about 1 to about 4 hours.

The condensation of Scheme 1 is capable of reaching a percent yield of at least about 10%, about 20%, about 30%, about 40%, about 50%, about 60%, about 70%, about 80%, or about 90% and/or up to about 90%, about 91%, about 95%, or more with a compound of Formula II or a compound of Formula III as limiting reagent present in an amount of from about 0.1 g to about 10 g, about 100 g, about 250 g, or about 500 g. The condensation of Scheme 1 is capable of reaching a percent yield of at least about 5%, about 10%, about 15%, about 20%, about 25%, about 30% and/or up to about 35%, about 45%, about 55%, about 65%, or more with a compound of Formula II or a compound of Formula III as limiting reagent present in an amount of from about 10 g to about 2 kg, about 100 g to about 1 kg, or about 500 g.

Another aspect of the invention comprises a method of synthesizing a compound of Formula I by condensing a compound of Formula II with a compound of Formula III to generate a compound of Formula IV and oxidizing the compound of Formula IV.

Formula I is:

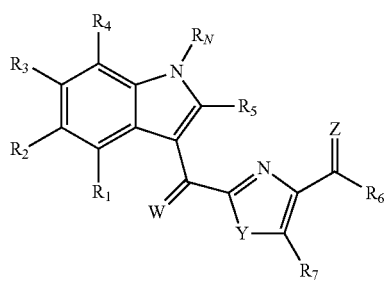

or a salt thereof,
wherein W, Y, Z, $R_1$-$R_7$, and $R_N$ are as defined above for Formula IV.

The synthesis of a compound of Formula I by condensing a compound of Formula II with a compound of Formula III to generate a compound of Formula IV and oxidizing the compound of Formula IV is shown below in Scheme 2:

Scheme 2

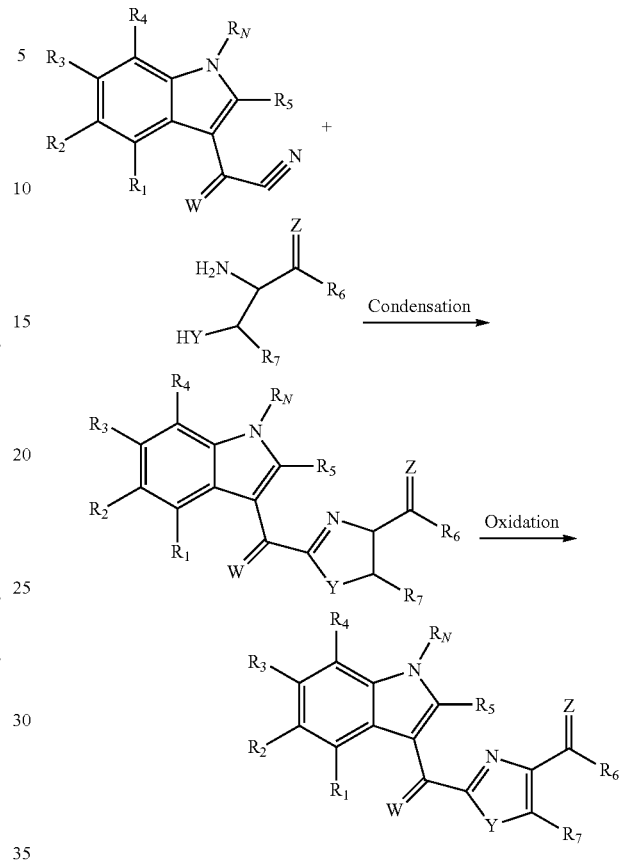

The condensation of Scheme 2 is preferably conducted in the presence of a base, in a solvent, at a temperature, and for a period of time as described above for the condensation of Scheme 1.

The oxidation of Scheme 2 is conducted in the presence of an oxidant (oxidizing agent). Any oxidizing agent is acceptable. Exemplary oxidants include air (atmosphere of the earth), 9-azabicyclo[3.3.1]nonane N-oxyl (ABNO), acetone, ammonium cerium (IV) nitrate, ammonium peroxydisulfate, 2-azaadamantane N-oxyl, 9-azabicyclo[3.3.1] nonane N-oxyl, 2-azaadamantane N-Oxyl (AZADO), 9-azanoradamantane N-oxyl, 1,4-benzoquinone, benzaldehyde, benzoyl peroxide, bleach, N-bromosaccharin, N-bromosuccinimide, (E)-but-2-enenitrile, N-fluoro-2,4,6-trimethylpyridinium triflate, N-tert-butylbenzenesulfinimidoyl chloride, tert-butyl hydroperoxide, tert-butyl hypochlorite, tert-butyl nitrite, cerium (IV) ammonium nitrate ($(NH_4)_2Ce(NO_3)_6$), chloramine-T, chloromethyl-4-fluoro-1,4-diazoniabicyclo[2.2.2]octane bis(tetrafluoroborate), 3-chloroperoxybenzoic acid, chromium compounds, chromium trioxide, Collins Reagent, Corey-Suggs Reagent, cumene hydroperoxide, copper compounds, crotononitrile, cumene hydroperoxide, 1,3-dibromo-5,5-dimethylhydantoin (DBDMH), 2,3-dichloro-5,6-dicyanobenzoquinone (DDQ), diethyl azodicarboxylate (DEAD), Dess-Martin periodinane, 1,8-diazabicyclo[5.4.0]undec-7-ene (DBU), diisopropyl azodicarboxylate (DIAD), 1,3-diiodo-5,5-dimethylhydantoin (DIH), dimethyl sulfoxide, di-tert-butyl peroxide, 3,3',5,5'-tetra-tert-butyldiphenoquinone (DPQ), (E)-but-2-enenitrile, ferric chloride, ferric nitrate, N-Fluoro-2,4,6-trimethylpyridinium triflate, formic acid, hydrogen peroxide, hydrogen peroxide urea adduct, hydroxy(tosyloxy)iodobenzene, hypervalent bromine compounds, hypervalent iodine compounds, iodine, iodobenzene dichloride, iodosobenzene bis (trifluoroacetate), iodosobenzene diacetate, N-iodosuccinimide, iodosylbenzene, 2-iodoxybenzoicacid, iron(III), iron (V), iron (IV), Jones Reagent, Koser's Reagent, magnesium monoperoxyphthalate hexahydrate, manganese compounds, manganese dioxide ($MnO_2$), manganese(IV) oxide, meta-chloroperbenzoic acid, N-methylmorpholine-N-oxide, methyltrioxorhenium, molybdenum compounds, N-bromosaccharin, N-bromosuccinimide, N-chloro tosylamide sodium salt, N-chlorosuccinimide, N-iodosuccinimide, N,N,N',N'-tetrachlorobenzene-1,3-disulfonamide, nitric acid, nitrosobenzene, N-methylmorpholine-N-oxide, N-tert-butylbenzenesulfinimidoyl chloride, osmium tetroxide, oxalyl chloride, oxone, oxygen, ozone, peracetic acid, periodic acid, peroxides, peroxy acids, phenyliodonium diacetate, pivaldehyde, potassium ferricyanide, potassium permanganate, potassium peroxydisulfate, potassium peroxomonosulfate, 2-propanone, pyridine N-oxide, pyridinium hydrobromide perbromide, pyridinium chlorochromate, pyridinium dichromate, pyridinium tribromide, ruthenium (III-VII) compounds, Sarett Reagent, Selectfluor, selenium dioxide, sodium bromate, sodium chlorite, sodium dichloroiodate, sodium hypochlorite, sodium nitrite, sodium perborate, sodium percarbonate, sodium periodate, sulfur, styrene, N-tert-butylbenzenesulfinimidoyl chloride, tert-butyl hydroperoxide, tert-butyl hypochlorite, tert-butyl nitrite, tetrabutylammonium peroxydisulfate, N,N,N',N'-tetrachlorobenzene-1,3-disulfonamide, 2,2,6,6-tetramethylpiperidinyloxy, tetrapropylammonium perruthenate, 3,3',5,5'-tetra-tert-butyldiphenoquinone, triacetoxyperiodinane, tribromoisocyanuric acid, trichloroisocyanuric acid, 1,1,1-trifluoroacetone, trifluoroacetic peracid, trimethylacetaldehyde, urea hydrogen peroxide adduct, vanadium compounds, and water, among others. Air, manganese dioxide, N-bromosuccinimide together with benzoyl peroxide, N-bromosuccinimide together with 1,8-diazabicyclo[5.4.0]undec-7-ene, and 1,8-diazabicyclo[5.4.0]undec-7-ene are preferred.

The oxidation of Scheme 2 is preferably conducted in a solvent as described above for the condensation of Scheme 1, except that dimethylformamide, tetrahydrofuran, dimethyl sulfoxide, dichloromethane, and pyridine are particularly preferred.

The oxidation of Scheme 2 is preferably conducted at a temperature of from about −10° C. to about 100° C., such as from about −10° C. to about 10° C., from about 30° C. to about 90° C., or other ranges therebetween.

The oxidation of Scheme 2 is preferably conducted for a period of time as described above for the condensation of Scheme 1. In some versions, the oxidation reaction is conducted for a period of from about 1 to about 20 hours.

Refluxing is preferably performed when conducting the oxidation of Scheme 2.

In some versions, the oxidation of Scheme 2 is performed after purifying the compound of Formula IV generated in the condensation reaction and subsequently mixing the purified compound of Formula IV with a solvent and oxidant as described above.

In other versions, the oxidation of Scheme 2 is performed in a "one-pot" synthesis without substantial isolation of the compound of Formula IV generated in the condensation reaction from the condensation reaction mixture. In the one-pot synthesis, the oxidant may be added directly to the condensation reaction mixture or the condensation mixture diluted with solvent without isolation or at least substantial isolation of any component therefrom. "Substantial isolation" refers to isolation of at least about 1%, about 2.5%, about 5%, about 10%, about 15%, about 20%, about 25%, about 30%, about 40%, about 50%, about 60%, about 70%, about 80%, or about 90% or more of any given component present in the condensation reaction mixture. Addition of any oxidant described above for the oxidation of Scheme 2 is acceptable. Oxidants selected from the group consisting of air, N-bromosuccinimide, N-bromosuccinimide together with 1,8-diazabicyclo[5.4.0]undec-7-ene, manganese dioxide are preferred.

In the one-pot synthesis, the condensation reaction mixture is preferably cooled from the condensation reaction temperature to a cooled temperature prior to, during, and/or just after adding the oxidant thereto. The cooled temperature is preferably at least about 5° C., about 10° C., about 15° C., about 20° C., about 25° C., about 30° C., or about 30° C. or more and/or up to about 45° C., about 50° C., about 60° C., about 70° C., about 80° C., about 90° C., about 100° C. or more lower than the condensation reaction temperature. The cooled temperature may be in a range from about −30° C. to about 30° C., such as about −20° C. to about 20° C., about −10° C. to about 10° C., or about −5° C. to about 5° C. The oxidant is preferably added when the condensation reaction mixture is at the cooled temperature.

The condensation reaction is preferably conducted for a period of at least about 0.5 hours, about 1 hour, about 2 hours, about 3 hours, about 4 hours, about 5 hours, about 7 hours, about 10 hours, about 12 hours, about 15 hours, about 17 hours, about 20 hours or more before the condensation reaction mixture is cooled to the cooled temperature.

The oxidation reaction may be conducted at the cooled temperature or may be conducted at an elevated temperature after reheating the reaction mixture from the cooled temperature. The elevated temperature may be at least about 5° C., about 10° C., about 15° C., about 20° C., about 25° C., about 30° C., or about 30° C. or more and/or up to about 45° C., about 50° C., about 60° C., about 70° C., about 80° C., about 90° C., about 100° C. or more greater than the cooled temperature. The elevated temperature may be in a range from about 10° C. to about 90° C., such as about 20° C. to about 80° C., or about 30° C. to about 70° C.

One or more solvents suitable for conducting the oxidation reaction may be added to the condensation reaction mixture prior to conducting the oxidation reaction. The one or more solvents may be added prior to, during, and/or just after adding the oxidant and may be added prior to, during, and/or just after the cooling. The one or more solvents are preferably added in an amount sufficient to dilute the condensation reaction mixture by an amount of at least about 1.1-fold, about 1.5-fold, about 2-fold, about 2.5-fold, about 5-fold, about 10-fold, about 15-fold, about 20-fold, about 25-fold, about 30-fold, or more and/or up to about 20-fold, about 30-fold, about 40-fold, about 50-fold, about 60-fold, about 70-fold, about 80-fold, about 90-fold, about 100-fold or more. The one or more solvents may comprise any one or combination of solvents described above for the condensation of Scheme 1. One or more solvents selected from the group consisting of dicholoromethane, pyridine, and dimethylformamide are preferred.

When N-bromosuccinimide with 1,8-diazabicyclo[5.4.0]undec-7-ene is used as the oxidant, the oxidation in one-pot synthesis is preferably conducted at a temperature of from about −10° C. to about 10° C., such as about 0° C., for a period of from about 0.5 hours to about 2 hours, such as about 1 hour. When manganese dioxide is used as the oxidant, the oxidation in one-pot synthesis is preferably conducted at a temperature of from about 30° C. to about 50° C., such as about 40° C., for a period of from about 4 to about 8 hours, such as about 6 hours. When air is used as the oxidant, the oxidation in one-pot synthesis is preferably conducted at a temperature of from about 50° C. to about 90° C., such as from about 60° C. to about 80° C., for a period of from about 0.5 to about 20 hours, such as from about 2 hours to about 12 hours.

Another aspect of the invention comprises a method of synthesizing a compound of Formula I by condensing a compound of Formula V with a compound of Formula VI. Formula V is:

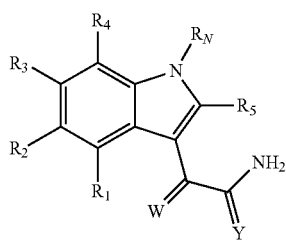

or a salt thereof,
wherein $R_1$-$R_5$, $R_N$, W, and Y are as defined above for Formula IV.
Formula VI is:

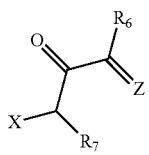

or a salt thereof,
wherein $R_6$, $R_7$, and Z are as defined above for Formula IV, and X is a leaving group.

The leaving group represented by X may be selected from the group consisting of chlorine (Cl), bromine (Br), iodine (I), —OS(O)$_2$CH$_3$ (mesylate, OMs), and —OS(O)$_2$C$_6$H$_4$CH$_3$ (tosylate, OTs), among others.

The synthesis of a compound of Formula I by condensing a compound of Formula V with a compound of Formula VI is shown below in Scheme 3:

Scheme 3

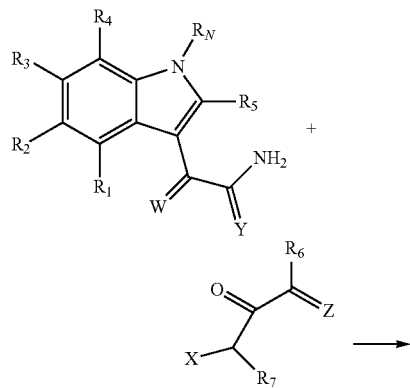

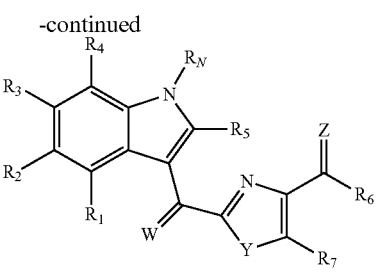

The condensation of Scheme 3 may be conducted in a solvent comprising a protic solvent, an aprotic solvent, or a mixture of a protic solvent and an aprotic solvent. The presence of a protic solvent is preferred. In some versions, the protic solvent comprises an alcohol. The alcohol in some versions is an aliphatic alcohol. The aliphatic alcohol may be a straight or branched short-chain alcohol (1-3 carbons), a straight or branched medium-chain alcohol (4-7 carbons), a straight or branched long-chain alcohol (8-21 carbons), or a straight or branched very long-chain alcohol (22 or more carbons). Exemplary alcohols include methanol, ethanol, n-butanol, isopropanol, phenol, 2,2,2-trifluoroethanol, ethylene glycol, glycerol, etc. In some versions, the protic solvent comprises an acid. The acid may comprise an organic acid. The organic acid may comprise a carboxylic acid, a sulfonic acid, or other acidic groups. Exemplary organic acids include formic acid, acetic acid, propionic acid, butyric acid, valeric acid, caproic acid, oxalic acid, lactic acid, malic acid, citric acid, benzoic acid, carbonic acid, and trifluoroacetic acid, among others. Other protic solvents include nitromethane, amines or alkyl amines such as diethyl amine, butyl amine, and propyl amine, ammonia, amides such as formamide, and water, among others. Various solvents or solvent combinations are suitable, such as an alcohol alone, an alcohol with water, an alcohol with an acid, an acid alone, an acid with water, an aprotic solvent alone, an aprotic solvent with an alcohol, an aprotic solvent with an acid, an aprotic solvent with an alcohol and an acid, an aprotic solvent with water, etc. Exemplary solvents include ethanol, methanol, methanol together with water, methanol together with acetic acid, acetic acid, isopropyl alcohol, dioxane, dioxane together with methanol, dioxane together with water, acetonitrile, ethyl acetate together with dimethylformamide, and ethyl acetate together with trimethylamine.

The condensation of Scheme 3 is preferably conducted at a temperature of from about 0° C. to about 80° C., such as from about 5° C. to about 75° C., from about 10° to about 70° C., from about 15° C. to about 75° C., or from about 20° C. to about 60° C. In some versions, the condensation of Scheme 3 is conducted at a temperature of from about 0° C. to about 40° C., such as from about 10° C. to about 30° C., from about 15° C. to about 25° C., or about 20° C. In some versions, the condensation of Scheme 3 is conducted at a temperature of from about 40° C. to about 80° C., such as from about 50° C. to about 70° C., from about 55° C. to about 65° C., or about 60° C.

The condensation of Scheme 3 is preferably conducted for a period of at least about 0.5, about 1, about 2, about 3, about 4 hours, or more and/or up to about 6 hours, about 7 hours, about 8 hours, about 9 hours, about 10 hours, about 15 hours, about 20 hours, about 25 hours, about 30 hours about 40 hours or more. In some versions, the condensation of Scheme 3 is conducted for a period of from about 0.5 to about 4 hours, such as from about 1 to about 3 hours.

Refluxing is preferably performed when conducting the condensing of Scheme 3.

The condensation of Scheme 3 is capable of reaching a percent yield of at least about 10%, about 20%, about 30%, about 40%, about 50%, about 60%, about 70%, about 80%, or about 90% and/or up to about 90%, about 91%, about 95%, or more with a compound of Formula V or a compound of Formula VI as limiting reagent present in an amount of from about 0.1 g to about 10 g, about 100 g, about 250 g, or about 500 g. The condensation of Scheme 3 is capable of reaching a percent yield of at least about 5%, about 10%, about 15%, about 20%, about 25%, about 30% and/or up to about 35%, about 45%, about 55%, about 65%, or more with a compound of Formula V or a compound of Formula VI as limiting reagent present in an amount of from about 10 g to about 2 kg, about 100 g to about 1 kg, or about 500 g.

The elements and method steps described herein can be used in any combination whether explicitly described or not.

The methods disclosed herein can comprise, consist of, or consist essentially of the essential elements and limitations of the method described herein, as well as any additional or optional ingredients, components, or limitations described herein or otherwise useful in synthetic organic chemistry.

All combinations of method steps as used herein can be performed in any order, unless otherwise specified or clearly implied to the contrary by the context in which the referenced combination is made.

As used herein, the singular forms "a," "an," and "the" include plural referents unless the content clearly dictates otherwise.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 5 to 6, from 1 to 9, from 3.6 to 4.6, from 3.5 to 9.9, and so forth.

All patents, patent publications, and peer-reviewed publications (i.e., "references") cited herein are expressly incorporated by reference to the same extent as if each individual reference were specifically and individually indicated as being incorporated by reference. In case of conflict between the present disclosure and the incorporated references, the present disclosure controls.

It is understood that the invention is not confined to the particular construction and arrangement of parts herein illustrated and described, but embraces such modified forms thereof as come within the scope of the claims.

EXAMPLES

The following examples show methods of synthesizing 2-(1'H-indole-3'-carbonyl)-thiazole-4-carboxylic acid methyl ester (ITE) as a model compound of Formula I. The examples are presented with reference to FIG. 1.

Example 1

Example 1 shows a method of synthesizing ITE from 1H-indole via a number of intermediates, as depicted in Scheme A of FIG. 1.

Intermediate 1 (ITE-1)

1H-indol-3-yl(oxo)acetyl Chloride

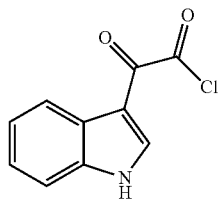 [SMILES: O=C(Cl)C(=O)c1c[nH]c2ccccc12]

1H-Indole (50 g, 0.43 mol.) and methyl tert-butyl ether (MTBE, 375 mL) were added to a three-necked round-bottom flask under stirring. The solution was cooled to −10° C., and then oxalyl chloride (56.9 g, 0.45 mol., 1.05 eq.) was added drop-wise while keeping the temperature between −10° C. and −5° C. The reaction mixture was then warmed to room temperature (~20° C.) and stirred at ~20° C. for 1 hour. Petroleum ether (PE, 375 mL) was added to the reaction mixture. The suspension was stirred at ~20° C. for 30 min. and then filtered. The filter cake was washed with PE (100 mL) and solvents in the cake were evaporated to give 108 g of product as a yellow solid. LC/MS: 208.6[M+1]

Intermediate 2 (ITE-2)

2-(1H-indol-3-yl)-2-oxoacetamide

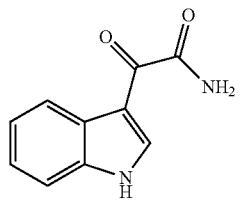 [SMILES: NC(=O)C(=O)c1c[nH]c2ccccc12]

ITE-1 (108 g, 0.52 mol.) was added portion-wise to a solution of concentrated ammonia (25%, w % in water, 354 g, 5.2 mol., 10 eq.) in ethanol (EtOH, 540 mL) at −5 to 14° C. After stirring for 2 hours at −5 to 14° C., the mixture was added to water (540 mL) and stirred at 20° C. for 30 min. The reaction mix was then filtered and the filter cake was washed with water (108 mL). The solvents in the cake were evaporated to give 68.5 g of product as an off-white solid (yield: 84.7%, two steps from 1H-indole). LC/MS: 189.1 [M+1]

Intermediate 3 (ITE-3)

1H-indol-3-yl(oxo)acetonitrile

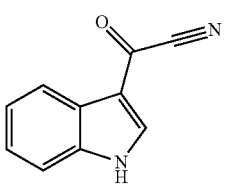 [SMILES: N#CC(=O)c1c[nH]c2ccccc12]

Pyridine (95.5 g, 1.21 mol., 3 eq.) as added to a solution of ITE-2 (68.5 g, 0.36 mol.) in ethyl acetate (EA, 1,000 mL) at 20° C. This was followed by addition of trifluoroacetic anhydride (TFAA, 126.8 g, 0.6 mol., 1.5 eq.) drop-wise at about 5-18° C. (room temperature, ~20° C., is acceptable) over 30 min. The mixture was stirred at about 5-18° C. (room temperature, ~20° C., is acceptable) for 1.5 hours, quenched with saturated aqueous sodium bicarbonate (700 mL), and stirred at 20° C. for 10 min. After a phase separation, the aqueous layer was extracted with EA (2×350 mL). The combined EA layers were washed with 0.5 N hydrochloric acid (2×350 mL) and then with saturated brine (350 mL). The organic layer was then dried over anhydrous Na$_2$SO$_4$ and concentrated to give 59 g of product as a pale brown solid (yield: 95.3%). LC/MS: 171.1[M+1]

Intermediate 4 (ITE-4)

2-(1'H-indole-3'-carbonyl)-4,5-dihydro-thiazole-4-carboxylic Acid Methyl Ester

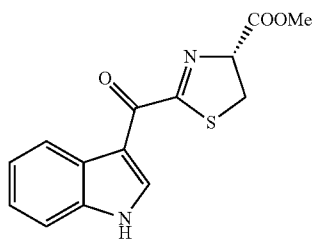 [SMILES: COC(=O)[C@@H]1CSC(C(=O)c2c[nH]c3ccccc23)=N1]

ITE-3 (1 g, 5.88 mmol.), L-cysteine methyl ester hydrochloride (1.01 g, 5.88 mmol., 1 eq.), 1,8-diazabicyclo[5.4.0]undec-7-ene (DBU, 90 mg, 0.587 mmol., 0.1 eq.), and N,N-dimethylformamide (DMF, 3 mL) were added to a three-necked round-bottom flask under stirring. After stirring at 40° C. for 1.5 hours, the reaction mixture was cooled to room temperature (~20° C.), and 30 mL of 1 N cold aqueous hydrochloric acid was added drop-wise under stirring. The suspension was filtered. The filter cake was washed with water (3×20 mL), and solvents in the cake were evaporated to give 1.56 g of product as a pale brown solid (yield: 90.63%, ITE-4 and ITE total). Dimethyl sulfoxide (DMSO), pyridine, and dioxane were also tested as solvents for the reaction with dioxane performing the worst overall. Other bases such as NaHCO$_3$, Na$_2$CO$_3$, and triethylamine (TEA) were tested and similar yields were obtained. Reaction temperatures of 25-28° C., 40-45° C., and 60-65° C. were tested and 40-45° C. was found to be optimal. Reaction durations of 1, 2, and 4 hours were tested and the results were similar except that the trace amount of starting material was still detectable in the 1 hour reaction. $^1$HNMR (400 MHz, d6-DMSO) δ 12.32 (brs, 1H), 8.63 (d, J=3.6 Hz, 1H), 8.19 (dd, J=6.8 Hz, 2.8 Hz, 1H), 7.55 (dd, J=6.4 Hz, 2.0 Hz, 1H), 7.31-7.25 (m, 2H), 5.66 (dd, J=10.4 Hz, 8.4 Hz, 1H), 3.76 (s, 3H), 3.67 (dd, J=11.6, 8.4 Hz, 1H), 3.52 (dd, J=10.4, 11.6 Hz, 1H). LC/MS: 289.1[M+1]

The Final Product (ITE): 2-(1'H-indole-3'-carbonyl)-thiazole-4-carboxylic Acid Methyl Ester

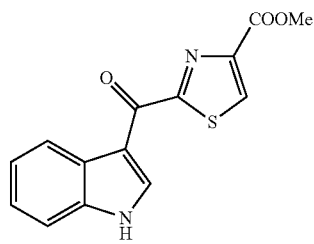 [SMILES: COC(=O)c1csc(C(=O)c2c[nH]c3ccccc23)n1]

Active manganese dioxide (1.51 g, 17.34 mmol., 5 eq.) was added to a solution of ITE-4 (1 g, 3.47 mmol.) in THF (tetrahydrofuran, 10 mL). After refluxing for 4 hours, the mixture was cooled to room temperature (~20° C.) and filtered through Celite. The filter cake was washed with 20 mL of hot THF (50-70° C.). The combined filtrates were concentrated in reduced pressure to give 0.84 g of product as a pale yellow solid (yield: 84.59%). Dichloromethane (DCM) and pyridine were also tested. DCM was not preferred due to the low solubility of ITE in the solvent. Pyridine was not preferred, especially when air was used as an oxidant due to its volatility. The air (atmosphere of the earth), manganese dioxide (MnO$_2$), N-bromosuccinimide (NBS) together with benzoyl peroxide (BPO), NBS together with 1,8-diazabicyclo[5.4.0]undec-7-ene (DBU), and DBU alone were tested as oxidant/s. The air and MnO$_2$ yielded better results with the former being more efficient. The reaction at 40° C. was also tested but refluxing shortened the reaction time. Durations of 1, 4, and 20 hours for the oxidation reaction were tested with 1 hour being not complete. $^1$HNMR (400 MHz, DMSO-d6) δ 12.38 (brs, 1H), 9.09 (s, 1H), 8.86 (s, 1H), 8.31-8.29 (m, 1H), 7.60-7.58 (m, 1H), 7.33-7.28 (m, 2H), 3.91 (s, 3H). LC/MS: 287.1[M+1]

Demonstration at a Scale of 0.5 kg

For large-scale synthesis of about 0.5 kg ITE from 1-H-indole, all steps of the process were similar to that described above for small-scale synthesis except for reagent amounts and the parameters described below. Maintaining temperature between −10° C. and −5° C. was noted as being important for reducing impurities when adding oxalyl chloride to the reaction of producing intermediate 1 (ITE-1). Three volumes of dimethylformamide (DMF) were used for the condensation reaction to produce intermediate 4 (ITE-4). The air (atmosphere of the earth) was used as an oxidant in the oxidation reaction to produce the final product (ITE) to further increase efficiency. The air was bubbled through the ITE-4 in 10 volumes of DMF at a flow rate of ~3 L/min while stirring at 80° C. for 10 hours. After cooling to room temperature, the reaction was added dropwise to 50 volumes of ice-cold water while stirring. The suspension was filtered. The filter cake was washed three times with 5 volumes of water each and then dried. The product was further purified by trituration in 5 volumes of methanol in reflux for 30 min. and filtration after cooling down to room temperature. Dimethyl sulfoxide (DMSO) was also tested in the oxidation reaction but performed worse than DMF. The oxidation reaction was tested at 60° C. but took longer to complete than that at 80° C. After the cyclization to make intermediate 4 (ITE-4) in DMF, a direct oxidation with air without work up (purification of ITE-4) was also tested at 60 and 80° C. for 2 to 12 hours but the impurities were higher than with the step-by-step procedure. The overall yield from indole to the final product (ITE) was around 30%, and the purity of the final product was 98.5% by HPLC (λ=214 nm). One batch of 490 g and another of 622 g were produced.

Example 2

Example 2 shows methods of synthesizing ITE from 1H-indol-3-yl(oxo)acetonitrile (ITE-3) in one container ("one-pot") without purification of intermediate 2-(1'H-indole-3'-carbonyl)-4,5-dihydro-thiazole-4-carboxylic acid methyl ester (ITE-4), as depicted in Scheme B of FIG. 1. The process is presented in two sets of conditions.

Example 2A

The Final Product (ITE): 2-(1'H-indole-3'-carbonyl)-thiazole-4-carboxylic Acid Methyl Ester

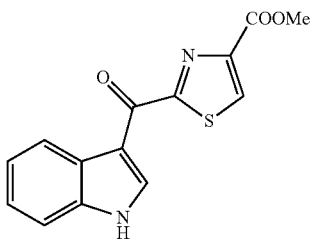 [SMILES: COC(=O)c1csc(C(=O)c2c[nH]c3ccccc23)n1]

ITE-3 (1 g, 5.88 mmol.), L-cysteine methyl ester hydrochloride (1.01 g, 5.88 mmol.), pyridine (5 mL) and 1,8-diazabicyclo[5.4.0]undec-7-ene (DBU, 90 mg, 0.587 mmol.) were added to a three-necked round-bottom flask under stirring. After stirring at 40° C. for 2 hours, the reaction mixture was diluted with dichloromethane (DCM, 140 mL), then cooled to 0°. To the mixture was added DBU (1.79 g, 1.18 mmol.), followed by N-bromosuccinimide (NBS, 1.15 g, 6.46 mmol.) portion-wise. After stirring at 0° C. for 1 hour, the mixture was quenched with 1N aqueous hydrochloric acid (100 mL) and extracted with DCM (20 mL) twice. The combined DCM layers were washed with 1N aqueous hydrochloric acid (50 mL) and brine (50 mL), dried over anhydrous $Na_2SO_4$, and concentrated to give 1.71 g of crude product as a pale yellow solid (yield: 86.9%). Dimethyl sulfoxide (DMSO) and $NaHCO_3$ were tested as solvent and base, respectively, for the condensation part of the reaction, and pyridine and DBU generated less impurity. A temperature for the condensation part of the reaction at 60° C. for the duration of 12 hours yielded comparable results.

Example 2B

The Final Product (ITE): 2-(1'H-indole-3'-carbonyl)-thiazole-4-carboxylic Acid Methyl Ester

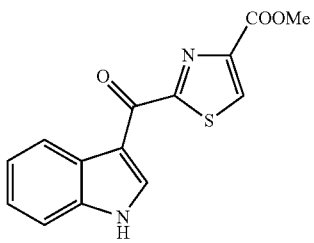 [SMILES: COC(=O)c1csc(C(=O)c2c[nH]c3ccccc23)n1]

ITE-3 (1 g, 5.88 mmol.), L-cysteine methyl ester hydrochloride (1.01 g, 5.88 mmol.), pyridine (5 mL) and 1,8-diazabicyclo[5.4.0]undec-7-ene (DBU, 90 mg, 0.587 mmol.) were added to a three-necked round-bottom flask under stirring. After stirring at 40° C. for 2 hours, the reaction mixture was diluted with dichloromethane (DCM, 140 mL), then cooled to 0° C. To the mixture was added pyridine (40 mL), followed by active manganese dioxide ($MnO_2$, 5.1 g, 58.76 mmol.). The mixture was stirred at 40° C. for 6 hours. The mixture was then cooled to room temperature (~20° C.) and filtered through Celite. The filter cake was washed with 20 mL of hot THF (50-70° C.). The filtrate was concentrated to give 1.64 g of crude product as a pale yellow solid (yield: 79.83%).

Example 3

Example 3 shows a method of synthesizing ITE from ITE-3 via intermediate 2-(1H-indol-3-yl)-2-oxoethanethioamide (ITE-4-A2), as depicted in Scheme C of FIG. 1.

Intermediate 4-A2 (ITE-4-A2)

2-(1H-indol-3-yl)-2-oxo-thioacetamide

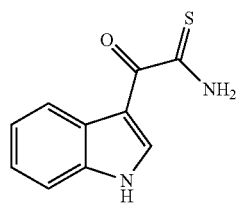 [SMILES: NC(=S)C(=O)c1c[nH]c2ccccc12]

To a solution of ITE-3 (1 g, 5.88 mmol.) in pyridine (10 mL) at 60° C. was added triethylamine (TEA, 654 mg, 6.46 mmol., 1.1 eq.), followed by ammonium sulfide solution (22%, w % in water, 3.64 g, 11.8 mmol., 2 eq.) drop-wise over 20 min. After stirring at 60° C. for 1.5 hours, the reaction mixture was diluted with 1N aqueous hydrochloric acid (50 mL) and ethyl acetate (EA, 50 mL). After a phase separation, the aqueous layer was extracted with EA (2×20 mL). The combined EA layers were washed with brine (50 mL), dried over anhydrous $Na_2SO_4$, and concentrated to give 1.3 g of crude product as a pale brown solid (yield: 93.9%). $^1$HNMR (400 MHz, DMSO-d6) δ 12.15 (brs, 1H), 10.20 (brs, 1H), 10.02 (brs, 1H), 8.18 (d, J=3.2 Hz, 1H), 8.13 (dd, J=6.4 Hz, 2.4 Hz, 1H), 7.53-7.51 (m, 1H), 7.28-7.23 (m, 2H). LC/MS: 205.1[M+1]

Methyl Bromopyruvate

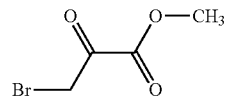

Methyl 2-oxopropanoate (50 g, 0.49 mol.) was added acetic acid (HOAc, 200 mL). Bromine (47 g, 0.59 mol.) was then added drop-wise at room temperature (RT, ~20° C.) over 50 min. The reaction was then stirred overnight at RT. The reaction was used directly in the next step.

The Final Product (ITE): 2-(1'H-indole-3'-carbonyl)-thiazole-4-carboxylic Acid Methyl Ester

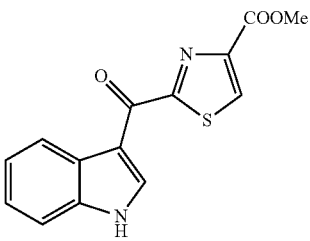 [SMILES: COC(=O)c1csc(C(=O)c2c[nH]c3ccccc23)n1]

ITE-4-A2 (100 mg, 0.5 mmol.) and the methyl bromopyruvate (108 mg, 0.6 mmol.) were added to methanol (MeOH, 5 ml). The reaction was stirred at 60° C. for 3 hours. The reaction mixture was poured into ice-cold water, and the solid was filtered and washed with water. The crude product was recrystallized in MeOH to give 75 mg of ITE (yield: 52%). Reaction conditions such as ethanol at 60° C., methanol together with water at 20° C., methanol together with acetic acid at reflux, acetic acid at 60° C., isopropyl alcohol at 60° C., dioxane at 20° C., dioxane together with methanol at 20° C., dioxane together with water at 20° C., acetonitrile at 20° C., ethyl acetate (EA) together with dimethylformamide (DMF) at 20° C., and EA together with triethylamine (TEA) at 20° C. were tested. While reaction in ethanol offers the best result, an ethyl ester of ITE analog, instead of methyl ester (ITE), is produced in addition to ITE and further manipulations are needed to convert the ethyl ester to ITE. Durations of 1, 3, and 4 hours were tested, and 1 to 3 hours was preferred.

CITED REFERENCES

J. Cheng, W. Li, B. Kang, Y. Zhou, J. Song, S. Dan, Y. Yang, X. Zhang, J. Li, S. Yin, H. Cao, H. Yao, C. Zhu, W. Yi, Q. Zhao, X. Xu, M. Zheng, S. Zheng, L. Li, B. Shen, and Y.-J. Wang, "Tryptophan derivatives regulate the transcription of Oct4 in stem-like cancer cells," *Nat. Commun.*, vol. 6, p. 7209, 2015.

H. Emtenäs, L. Alderin, and F. Almqvist, "An enantioselective ketene-imine cycloaddition method for synthesis of substituted ring-fused 2-pyridinones," *J. Org. Chem.*, vol. 66, no. 20, pp. 6756-6761, October 2001.

P. Grzywacz, R. R. Sicinski, and H. F. DeLuca, "A Concise Synthesis of an AHR Endogenous Ligand with the Indole-carbonylthiazole Skeleton," *HETEROCYCLES*, vol. 60, no. 5, p. 1219, 2003.

W. A. Loughlin, S. A. Knevitt, R. E. Hosking, and R. L. Marshall, "Approaches to the High-Throughput Synthesis of Analogues of Dihydroaeruginoic Acid," *Aust. J. Chem.*, vol. 53, no. 6, pp. 457-462, January 2000.

M. Narender, M. S. Reddy, R. Sridhar, Y. V. D. Nageswar, and K. R. Rao, "Aqueous phase synthesis of thiazoles and aminothiazoles in the presence of β-cyclodextrin," *Tetrahedron Lett.*, vol. 46, no. 35, pp. 5953-5955, August 2005.

L. F. Nugent, G. Shi, B. P. Vistica, O. Ogbeifun, S. J. H. Hinshaw, and I. Gery, "ITE, A Novel Endogenous Nontoxic Aryl Hydrocarbon Receptor Ligand, Efficiently Suppresses EAU and T-Cell-Mediated Immunity," *Invest. Ophthalmol. Vis. Sci.*, vol. 54, no. 12, pp. 7463-7469, 2013.

T. M. Potewar, S. A. Ingale, and K. V. Srinivasan, "Efficient synthesis of 2,4-disubstituted thiazoles using ionic liquid under ambient conditions: a practical approach towards the synthesis of Fanetizole," *Tetrahedron*, vol. 63, no. 45, pp. 11066-11069, November 2007.

F. J. Quintana, G. Murugaiyan, M. F. Farez, M. Mitsdoerffer, A.-M. Tukpah, E. J. Burns, and H. L. Weiner, "An endogenous aryl hydrocarbon receptor ligand acts on dendritic cells and T cells to suppress experimental autoimmune encephalomyelitis," *Proc. Natl. Acad. Sci. U.S.A.*, vol. 107, no. 48, pp. 20768-20773, November 2010.

J. Song, M. Clagett-Dame, R. E. Peterson, M. E. Hahn, W. M. Westler, R. R. Sicinski, and H. F. DeLuca, "A ligand for the aryl hydrocarbon receptor isolated from lung," *Proc. Natl. Acad. Sci. U.S.A.*, vol. 99, no. 23, pp. 14694-9, November 2002.

K. Wang, Y. Li, Y.-Z. Jiang, C.-F. Dai, M. S. Patankar, J.-S. Song, and J. Zheng, "An Endogenous Aryl Hydrocarbon Receptor Ligand Inhibits Proliferation and Migration of Human Ovarian Cancer Cells," *Cancer Lett.*, July 2013.

We claim:

1. A method of synthesizing a compound comprising condensing a compound of Formula II with a compound of Formula III to yield a compound of Formula IV, wherein:

Formula II is:

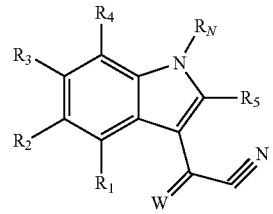

or a salt thereof;

Formula III is:

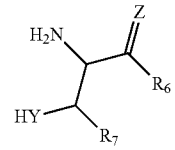

or a salt thereof;

Formula IV is:

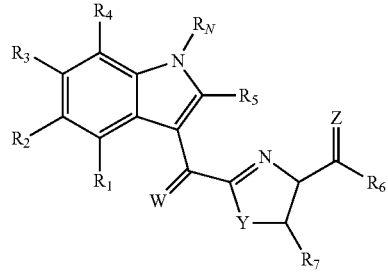

or a salt thereof;

W, Y, and Z are each independently selected from the group consisting of oxygen (O) and sulfur (S); and $R_1$, $R_2$, $R_3$, $R_4$, $R_5$, $R_6$, $R_7$, and $R_N$ are each independently selected from the group consisting of hydrogen, deuterium, halo, amino, hydroxy, cyano, formyl, nitro, alkyl, haloalkyl, alkenyl, haloalkenyl, alkynyl, haloalkynyl, alkoxy, haloalkoxy, thioalkoxy, halothioalkoxy, alkanoyl, haloalkanoyl, thioalkanoyl, halothioalkanoyl, carbonyloxy, halocarbonyloxy, carbonylthio, halocarbonylthio, thiocarbonyloxy, halothiocarbonyloxy, thiocarbonylthio, halothiocarbonylthio, and —S(O)$_n$R$_8$ (n=0 to 2, $R_8$ is directly connected to S), wherein $R_8$ is selected from the group consisting of hydrogen, deuterium, halo, amino, hydroxy, thiol, cyano, formyl, alkyl, haloalkyl, alkenyl, haloalkenyl, alkynyl, haloalkynyl, alkoxy, haloalkoxy, thioalkoxy, halothioalkoxy, alkanoyl, haloalkanoyl, thioalkanoyl, halothioalkanoyl, carbonyloxy, halocarbonyloxy, carbonylthio, halocarbonylthio, thiocarbonyloxy, halothiocarbonyloxy, thiocarbonylthio, and halothiocarbonylthio.

2. The method of claim 1 wherein the condensing is conducted in the presence of an aprotic solvent.

3. The method of claim 2 wherein the aprotic solvent is selected from the group consisting of N,N-dimethylformamide, dimethyl sulfoxide, pyridine, and dioxane.

4. The method of claim 1 wherein the condensing is conducted in the presence of a base.

5. The method of claim 4 wherein the base is selected from the group consisting of 1,8-diazabicyclo[5.4.0]undec-7-ene, $NaHCO_3$, $Na_2CO_3$, and triethylamine.

6. The method of claim 1 wherein the condensing is conducted at a temperature of from about 25° C. to about 65° C.

7. The method of claim 1 further comprising oxidizing the compound of Formula IV to yield a compound of Formula I, wherein Formula I is:

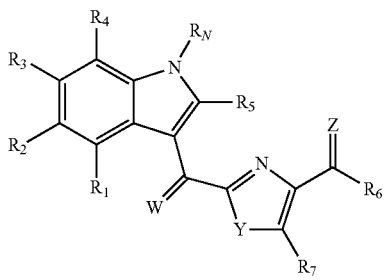

or a salt thereof.

8. The method of claim 7 wherein the oxidizing is conducted in the presence of an oxidant selected from the group consisting of air, manganese dioxide, N-bromosuccinimide, 1,8-diazabicyclo[5.4.0]undec-7-ene, N-bromosuccinimide together with benzoyl peroxide, and N-bromosuccinimide together with 1,8-diazabicyclo[5.4.0]undec-7-ene.

9. The method of claim 7 wherein the oxidizing is conducted in the presence of a solvent selected from the group consisting of dimethylformamide, tetrahydrofuran, dimethyl sulfoxide, dichloromethane, and pyridine.

10. The method of claim 7 wherein the oxidizing is conducted at a temperature of from about 30° C. to about 90° C.

11. The method of claim 7 wherein the oxidizing is conducted without substantial isolation of the compound of Formula IV from a reaction mixture in which the compound of Formula IV was synthesized.

12. The method of claim 11 wherein the oxidizing comprises adding an oxidant directly to the reaction mixture or a diluted reaction mixture comprising the reaction mixture diluted with solvent.

13. The method of claim 11 further comprising, after the condensing and prior to the oxidizing, diluting the reaction mixture by an amount of at least about 2-fold.

14. The method of claim 11 further comprising, after the condensing and prior to the oxidizing, cooling the reaction mixture or a diluted reaction mixture comprising the reaction mixture diluted with solvent from a condensation reaction temperature at which the condensing is conducted to a cooled temperature, wherein the cooled temperature is at least about 10° C. lower than the condensation reaction temperature.

15. The method of claim 14 further comprising adding an oxidant to the reaction mixture or the diluted reaction mixture when the reaction mixture or the diluted reaction mixture is at the cooled temperature.

16. The method of claim 14 wherein the oxidizing is conducted at the cooled temperature.

17. The method of claim 15 further comprising, after the cooling, heating the reaction mixture or the diluted reaction mixture from the cooled temperature to a heated temperature and conducting the oxidizing at the heated temperature, wherein the heated temperature is at least about 10° C. higher than the cooled temperature.

18. A method of synthesizing a compound comprising condensing a compound of Formula V with a compound of Formula VI to yield a compound of Formula I, wherein:
Formula V is:

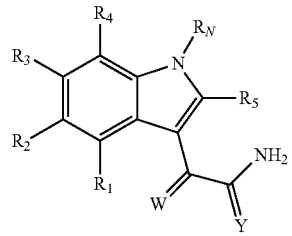

or a salt thereof;
Formula VI is:

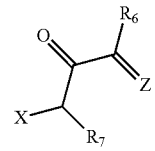

or a salt thereof;
Formula I is:

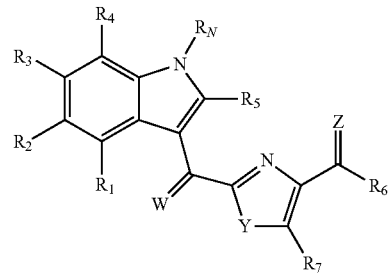

or a salt thereof;
X is a leaving group;
W, Y, and Z are each independently selected from the group consisting of oxygen (O) and sulfur (S); and
$R_1$, $R_2$, $R_3$, $R_4$, $R_5$, $R_6$, $R_7$, and $R_N$ are each independently selected from the group consisting of hydrogen, deuterium, halo, amino, hydroxy, cyano, formyl, nitro, alkyl, haloalkyl, alkenyl, haloalkenyl, alkynyl, haloalkynyl, alkoxy, haloalkoxy, thioalkoxy, halothioalkoxy, alkanoyl, haloalkanoyl, thioalkanoyl, halothioalkanoyl, carbonyloxy, halocarbonyloxy, carbonylthio, halocarbonylthio, thiocarbonyloxy, halothiocarbonyloxy, thiocarbonylthio, halothiocarbonylthio, and —S(O)$_n$R$_8$ (n=0 to 2, R$_8$ is directly connected to S), wherein R$_8$ is selected from the group consisting of hydrogen, deuterium, halo, amino, hydroxy, thiol, cyano, formyl, alkyl, haloalkyl, alkenyl, haloalkenyl, alkynyl, haloalkynyl, alkoxy, haloalkoxy, thioalkoxy, halothioalkoxy, alkanoyl, haloalkanoyl, thioalkanoyl, halothioalkanoyl, carbonyloxy, halocarbonyloxy, carbonylthio, halocarbonylthio, thiocarbonyloxy, halothiocarbonyloxy, thiocarbonylthio, and halothiocarbonylthio; and wherein the condensing is conducted in a protic solvent.

19. The method of claim 18 wherein X is selected from the group consisting of chlorine (Cl), bromine (Br), iodine (I), —OS(O)$_2$CH$_3$, and —OS(O)$_2$C$_6$H$_4$CH$_3$.

20. The method of claim 18, wherein the condensing is conducted in a solvent selected from the group consisting of an alcohol, an alcohol together with water, an alcohol together with an acid, an acid, an alcohol together with an aprotic solvent, or water together with an aprotic solvent.

21. The method of claim 18, wherein the condensing is conducted at a temperature of about 50° C. to about 70° C.

22. The method of claim 1, wherein R$_N$ is an amino protecting group.

23. The method of claim 22, wherein the amino protecting group forms a group selected from the group consisting of an alkyl carbamate, allyl carbamate (Alloc), t-butyl carbamate (BOC), 9-fluorenylmethyl carbamate (FMOC), benzyl carbamate (Cbz), acetamide, chloroacetamide, trifluoroacetamide (TFA), phthalimide, benzylamine, triphenylmethylamine (tritylamine), benzylideneamine, p-toluenesulfonamide, and tosylamide.

24. The method of claim 18, wherein R$_N$ is an amino protecting group.

25. The method of claim 24, wherein the amino protecting group forms a group selected from the group consisting of an alkyl carbamate, allyl carbamate (Alloc), t-butyl carbamate (BOC), 9-fluorenylmethyl carbamate (FMOC), benzyl carbamate (Cbz), acetamide, chloroacetamide, trifluoroacetamide (TFA), phthalimide, benzylamine, triphenylmethylamine (tritylamine), benzylideneamine, p-toluenesulfonamide, and tosylamide.

* * * * *